United States Patent
Wachs

(10) Patent No.: US 6,198,005 B1
(45) Date of Patent: *Mar. 6, 2001

(54) TREATING METHANOL CONTAINING WASTE GAS STREAMS

(75) Inventor: Israel E. Wachs, Bridgewater, NJ (US)

(73) Assignee: Lehigh University, Bethlehem, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/294,365

(22) Filed: Apr. 20, 1999

Related U.S. Application Data

(60) Provisional application No. 60/082,750, filed on Apr. 23, 1998.

(51) Int. Cl.$^7$ .................................................. C07C 45/29
(52) U.S. Cl. .................... 568/472; 568/449; 502/350; 585/638; 585/640; 423/415.1; 423/512.1
(58) Field of Search .............................. 568/472, 449; 502/350; 585/638, 640; 423/415.1, 512.1

(56) References Cited

U.S. PATENT DOCUMENTS

| | | | |
|---|---|---|---|
| 4,544,649 | 10/1985 | Wachs | 502/350 |
| 4,814,541 | 3/1989 | Lewis | 585/640 |
| 4,861,938 | 8/1989 | Lewis et al. | 585/640 |
| 4,873,390 | 10/1989 | Lewis et al. | 585/638 |
| 4,973,792 | 11/1990 | Lewis et al. | 585/638 |
| 5,157,181 | 10/1992 | Stine et al. | 585/329 |
| 5,176,897 | 1/1993 | Lester | 423/659 |
| 5,292,704 | 3/1994 | Lester | 502/309 |
| 5,907,066 | 5/1999 | Wachs | 568/472 |

FOREIGN PATENT DOCUMENTS

| | | |
|---|---|---|
| 0 068 377 | 1/1983 | (EP). |
| 0 267 711 | 5/1988 | (EP). |
| 589292 | 6/1947 | (GB). |
| 1263139 | 2/1972 | (GB). |
| 8 002 177-7 | 9/1981 | (SE). |
| 212993 | of 0000 | (SU). |

OTHER PUBLICATIONS

Garner, "Methanol Emission Control Options Meet EPA 'Cluster' Requirement," Pulp & Paper, 59–62, 1996.
Arora, et al., "Surface Aspects of Bismuth–Metal Oxide Catalysts," Journals of Catalysis, 159, 1–13, 1996.
Hardcastle, et al. "Determination of Molybdenum–Oxygen Bond Distances and Bond Orders by Raman Spectroscopy," J. Ramen Spectroscopy, 21, 683–691, 1990.
Hardcastle, et al., "Determination of Vanadium–Oxygen Bond Distances and Bond Orders by Raman Spectroscopy," Journal Physical Chemistry, 95(13) 5031–5041, 1991.
Hardcastle, et al., "Determination of Niobium–Oxygen Bond Distances and Bond Orders by RamanSpectroscopy," Solid State Ionics, 45, 201–213, 1991.
Hardcastle, et al., "Determination of the Molecular Structures of Tungstates by Raman Spectroscopy," J. Ramen Spectoroscopy, 26, 397–405, 1995.
Weckhuysen, et al., "Raman Spectroscopy of Supported Chromium Oxide Catalyst," J. Chem., Coc. Faraday Faraday Trans., 92(11), 1969–1973, 1996.
Weigand, et al., "Model Studies of the Desulfurization Reactions on Metal Surfaces and in Organometallic Complexes," Chemical Reviews, vol. 92, No. 4, pp. 491–504, 1992.
Nichols, et al., "EPA's Proposed Cluster Rules Shape U.S. Paper Industry's Near Future," Pulp & Paper, 75–85, 1994.
Yang, et al., "Hydrogen Recovery from Hydrogen Sulfide by Oxidation and By Decomposition," Ind. Eng. Chem. Res., 33, 1090–1097, 1994.
Mehta, "Unbleached Mills won't Escape Impact of EPA's 'Cluster Rules'," Pulp & Paper, 61–70, 1995.
Barnes, et al., "Molybdena on Silica Catalysts: Role of Preparation Methods on the Structure—Selectivity Properties for the Oxidation of Methanol," Journal of Catalysis, 150, 407–420, 1994.
N.N. Sazonova, et al., "Relationship Between Sulfur Dioxide Oxidation and Selective Catalytic No Reduction by Ammonia on $V_2O_5$–$TiO_2$ Catalysts Doped With $WO_3$ and $Nb_2O_5$," React. Kinet. Catal. Lett., Vol. 52, No. 1, 101–106, 1994.
Deo, et al., "Physical and Chemical Characterization of Surface Vanadium Oxide Supported on Titania: Influence of the Titania Phase (Anatase, Rutile, Brookite and B)," Applied Catalysis A: General, 91, 27–42, 1992.
Deo, et al., "Effect of Additives on the Structure and Reactivity of the Surface Vanaidum Oxide Phase In V2O5/TiO2 Catalysts," Journal of Catalysis, 146, 335–345, 1994.
Kim, et al., "Molecular Structures and Reactivity of Supported Molybdenum Oxide Catalysts," Journal of Catalysis, 146, 268–277, 1994.
Kiadó, Relationship Between Sulfur Dioxide Oxidation and Selective Catalytic No Reduction by Ammonia on V2O5–TiO2 Catalysts Doped with WO3 and Nb205, React. Kinet. Catal. lett., 52, No. 1, 101–106, 1994.
Jehng, et al., "The Molecular Structures and Reactivity of V2O5/TiO2/SiO2 Catalysts," Catalysts Letters, 13, 9–20, 1992.
"Odor control: Location, Process Determines Nuisance Level," Pulp & Paper, 147–148, 1995.

*Primary Examiner*—Sreeni Padmanabhan
(74) *Attorney, Agent, or Firm*—Banner & Witcoff, Ltd.

(57) ABSTRACT

A method wherein a methanol-containing waste gas stream, such as a pulp mill waste stream which contains methanol and other waste products, including methyl mercaptans, is passed in contact with a catalyst comprising a supported or unsupported bulk metal oxide catalyst in the presence of an oxidizing agent; preferably the gas stream is contacted with the catalyst, in the presence of the oxidizing agent, for a time sufficient to convert at least a portion of the methanol to formaldehyde ($CH_2O$).

18 Claims, No Drawings

TREATING METHANOL CONTAINING WASTE GAS STREAMS

This application claims the priority benefits from the U.S. provisional application Serial No. 60/082,750 filed Apr. 23, 1998.

BACKGROUND OF THE INVENTION

1. Field of the Invention

This invention broadly relates to a process for treating methanol-containing waste gas streams, such as encountered in a paper (pulp) mill. More particularly, this invention provides a method wherein a gas stream, such as from a paper pulp mill containing methanol, and other waste products, including methyl mercaptans, is passed in contact with a catalyst comprising a supported or unsupported bulk metal oxide in the presence of an oxidizing agent. In a preferred embodiment, the gas stream is contacted with the catalyst, in the presence of the oxidizing agent, for a time sufficient to convert at least a portion of the methanol to formaldehyde ($CH_2O$).

2. Description of Related Art

Pulp mills that chemically digest wood sources, such as by using the Kraft process, generate a significant amount of by-product methanol, in addition to other potential pollutants such as reduced sulfur compounds, higher alcohols, terpenes, acetone, amines, acetaldehyde and methyl ethyl ketone. Significant methanol emissions are encountered during the overall pulping and paper-making operation, particularly from the following pulp mill sub-systems: pulp digesters, blow heat recovery units, and multiple-effect evaporators. In the past, this methanol was often discharged into the air or directly into wastewater. With growing environmental concerns over pollution caused by these past practices, however, more stringent emission requirements have evolved. As a consequence, processes must be developed to dispose of the methanol, and the other pulp mill by-products, in a more environmentally satisfactory manner. At the present time, two alternatives have been suggested as being suitable for complying with regulatory standards. Garner, Jerry, *Pulp & Paper*, (August 1996):59–62. In both approaches, the various waste steams generated in a pulp mill containing by-product methanol, and a variety of the other noted compounds, are first consolidated into a single condensate stream.

In a first alternative, this consolidated condensate stream is fed to a steam stripping column which is operated in a way to remove and concentrate, in the gas phase, a major portion of the pollutants from the liquid condensate. Over 80–90% of the methanol of the consolidated feed steam is removed in the stripping column, while the methanol concentration is increased from about 0.1–0.5% in the liquid feed to about 35–55% in the steam stripper gaseous overhead.

This methanol-containing stripper overhead is then treated by indiscriminate (noncatalytic) oxidation (incineration) to produce a waste gas that can be safely discharged into the environment. To safely complete the oxidation of the gas constituents, the incineration process must be operated at temperatures approaching 1000° C. Such operation generally requires the use of an auxiliary fuel source. In some facilities, the fuel value of the stripper overhead is recovered by using it, for example, to power a boiler or a lime kiln. In some cases, the methanol content of the stripper overhead is further concentrated by distillation to increase its value before use as a fuel.

The second alternative delivers the condensate stream to a wastewater treatment system where aerobic microorganisms use the methanol as a carbon source, converting it to carbon dioxide and water.

While highly dependent on the wood source and the basic operating conditions of a pulp mill, the consolidated waste methanol stream or condensate from a pulp mill can be expected to contain, among other materials, methanol and other higher alcohols, methyl ethyl ketone, acetaldehyde, acetone, terpenes, amines, ammonia and reduced sulfur compounds. The concentration of these materials in the aqueous condensate is enriched by steam stripping and results in a gas stream which typically contains about 40–55 wt. % methanol, 2–8 wt. % higher alcohols, such as ethanol and isopropanol, 2–8 wt. % ketones, including methyl ethyl ketone, methyl isobutyl ketone and acetone, 1–3 wt. % reduced sulfur compounds including hydrogen sulfide and methyl mercaptans, such as methanethiol ($CH_3SH$), dimethyl sulfide ($CH_3SCH_3$) and dimethyl disulfide ($CH_3SSCH_3$), about 1–2 wt. % amines, including ammonia, 1–6 wt. % terpenes, such as α-pinene and α-terpineol, and the balance (generally 40–50 wt. %) water.

Simply incinerating or biologically degrading this methanol-containing waste stream constitutes a costly and inefficient use of the inherent resources present in the stream. While procedures used to recover the fuel value of the stream seek to reduce such inefficiencies, they create their own source of problems. In particular, the variable nature of the methanol-containing stream creates the risk of operational upsets in the operation of the lime kiln or a boiler. Further, if the lime kiln or boiler operation is interrupted, then the operation of the stripper must be discontinued since there is no way to dispose the concentrated stripper overhead. As a result of these potential problems, a pulp mill likely would need to operate with a dedicated incinerator using a power boiler as back-up.

In its preferred aspects, the present invention is directed to an improved process for using by-product methanol from methanol-containing waste streams, such as encountered in a paper (pulp) mill, to produce a valuable chemical commodity, formaldehyde.

BRIEF DESCRIPTION OF THE INVENTION

This invention provides a method wherein a methanol-containing waste gas stream, such as originates from a paper pulp mill, and containing other waste products, including methyl mercaptans, is contacted, under oxidizing conditions, with a catalyst comprising a bulk metal oxide. The bulk metal oxide catalyst can be either unsupported, or supported. The gas is preferably passed in contact with the catalyst in the presence of an oxidizing agent for a time sufficient to convert at least a portion of the methanol to formaldehyde ($CH_2O$), and then recovering the formaldehyde as a product stream separate from the gas stream. In an alternative embodiment, the gas can be contacted with the catalyst for a time sufficient, and under oxidizing conditions sufficient, to oxidize the carbon-containing oxidizable components of the gas stream, including methanol, completely to carbon oxides ($CO_x$) and the sulfur-containing components to sulfur oxides ($SO_x$).

The oxidizing conditions can be established using an oxidizing agent such as oxygen or air. In the presence of the catalyst, other volatile organic compounds beside methanol are also oxidized, amines are generally reduced to nitrogen (though some portion may be oxidized to nitrogen oxides) and the sulfur is oxidized to $SO_2$, and possibly a minor amount of $SO_3$.

Accordingly, a preferred embodiment of the present invention is directed to a process for producing formaldehyde from methanol-containing waste gas streams, especially pulp mill condensates, which comprises (1) producing a methanol-containing gas from the condensate, such as by steam stripping the pulp mill condensates, (2) contacting said methanol-containing waste gas with a bulk metal oxide catalyst under oxidizing conditions for a time sufficient to convert at least a portion of the methanol to formaldehyde, and (3) recovering said formaldehyde from the gas stream. Following removal of the formaldehyde, the residual gas stream likely will be sent to an incinerator or after-burner for complete combustion of the residual impurities and products so as to produce a gas suitable for direct discharge into the atmosphere.

In carrying out the process of the present invention, known bulk metal oxide catalysts can be used. The catalyst can either be unsupported, or supported. Such catalysts generally constitute molybdates (Mo), chromates (Cr), vanadates (V), rhenates (Re), titinates (Ti), niobates (Nb), tungstates (W), antimonates (Sb), stannates (Sn), ceriates (Ce) and mixtures thereof. Such metal oxides also contain a wide variety of other metal species such as alkali metals (such as sodium (Na), lithium (Li), potassium (K) and cesium (Cs)), alklaine earth metals (such as calcium (Ca), barium (Ba), and magnesium (Mg)) and transition metals (such as copper (Cu), nickel (Ni), cobalt (Co), aluminum (Al), lead (Pb), bismuth (Bi), iron (Fe), zinc (Zn), cadmium (Cd), tellurium (Te), manganese (Mn)). Those skilled in the art recognize the wide variety of available bulk metal oxide catalysts.

The bulk metal oxide catalyst compositions useful for practicing the present invention are known in the prior art.

DETAILED DESCRIPTION OF THE INVENTION

In accordance with the present invention, a methanol-containing waste gas stream, such as a pulp mill waste gas stream containing methanol, and containing a variety of other components including higher alcohols, methyl ethyl ketone, methyl isobutyl ketone, acetaldehyde, acetone, terpenes, amines, ammonia and reduced sulfur compounds, is treated by contacting the waste gas stream, under an oxidizing condition, with a bulk metal oxide catalyst. The catalyst can either be unsupported, or supported on a substrate. Such a gas can be obtained from a kraft pulp mill by steam stripping the condensate stream consolidated from a variety of pulp mill processing steps. Depending upon the contacting conditions, such as the nature of the catalyst, the temperature, the catalyst loading and the like, the constituents of the waste gas stream may be partially or completely oxidized. Preferably, the conditions are selected to facilitate partial oxidation of at least the methanol in the stream to formaldehyde. Importantly, the partial oxidation of methanol to formaldehyde using the catalysts of the present invention is not adversely affected by the presence of a large amount of water, which typically comprises 40–50 wt. % of the gas stream, a significant amount of reduced sulfur compounds, such as hydrogen sulfide and methyl mercaptans, and amines, found in the pulp mill condensates. Methanol can be oxidized selectively to formaldehyde in the presence of this large amount of water and reduced sulfur compounds.

In accordance with the present invention, the waste gas stream containing the methanol and other oxidizable carbon and sulfur-based constituents contacts the bulk metal oxide catalyst under oxidizing conditions at a temperature in the range of 200° to 700° C., preferably in the range of 300° to 600° C. and most often in the range of 325° to 500° C. The oxidizing agent can usually be oxygen or air. In the preferred approach, the contacting of the methanol-containing pulp mill waste gas with the bulk metal oxide catalyst under an oxidizing atmosphere, e.g., in the presence of oxygen, and at an appropriate temperature, causes a selective conversion of the methanol to formaldehyde. The oxidizable constituents of the gaseous feed stream generally will comprise at least about 0.1 mole %, and preferably at least 1.0 mole % and higher of methanol, although higher concentrations may be employed. The gas stream will also include many other oxidizable or inert constituents. For illustrative purposes only, for example, other oxidizable components of the gas stream may include hydrogen sulfide, methyl mercaptans, terpenes, acetone, methyl ethyl ketone, amines and higher alcohols. The gas stream may also include water. The gas stream preferably contacts the catalyst at a temperature of about 325° to 450° C.

The waste gas or any of its precursor streams, e.g., the consolidated pulp mill condensate, may optionally be treated to reduce the concentration of constituents that may cause rapid fouling of the catalytic surface or any catalyst support surface. For example, higher concentration of terpenes, e.g., concentrations above 500–1000 ppm, have demonstrated a tendency to cause carbon deposition on some catalyst surfaces. In the case of a pulp mill waste stream, the terpene concentration in the gas depends on the severity of the pulp mill concentrate vaporization conditions. This carbon can be easily burned off (removed by oxidization from) the catalyst and any support to restore the catalytic activity of the catalyst. However, to avoid frequent interruptions in the operation of the catalytic reactor for regenerating the catalyst, it may be preferred in some applications to reduce the concentration of such carbon-forming constituents below such concentrations.

To achieve high selectivity in the conversion of methanol, contained for example in a pulp mill waste gas stream, to formaldehyde, it is important to maintain the flow rate of the gas stream to provide an amount of methanol per unit mass of catalyst in the range of $10^{-2}$ to $10^5$ cubic centimeters of methanol (assessed under standard conditions of temperature and pressure (STP)) per gram of active catalyst per minute (excluding inert ceramic components or other inert catalyst support material). Given the typical composition of the pulp mill waste gas, such conditions will also facilitate proper oxidation of the other components of the gas stream as well. Generally, higher reaction temperatures permit higher flow rates. Usually, the process can be operated at 0.1 to $10^4$, cubic centimeters (STP) of methanol per gram of catalyst per minute.

As used herein, the term "selectively" is intended to embrace the conversion of at least 1% of the methanol, preferably at least 10% of the methanol, more usually at least 50% of the methanol and most often at least 70%, and most preferably 95% of the methanol which contacts the catalyst, to formaldehyde. Selectivity, as that term is used herein, is determined by dividing the moles of formaldehyde in the methanol conversion products by the moles of methanol converted (consumed) from the feed to the reactor.

The oxidation reaction is exothermic. As recognized by those skilled in the art, a variety of reactor designs may be employed to accommodate the necessary mass and heat transfer processes for effective operation of the process on a continuous basis. The reaction may be conducted at atmosphere pressure and above, or below atmospheric pressure.

Formaldehyde is the intended product and it can be recovered from the gaseous reaction products using any one of a number of ways known to those skilled in the art.

As will be recognized by those skilled in the art, the gases leaving the reactor may contain unreacted starting products, including inert gases that may have been added, as well as formaldehyde and water. The principal by-product that is formed during the partial oxidation of methanol is carbon monoxide, which may be accompanied by a small amount of carbon dioxide. Oxidation of the other usual constituents in the pulp mill waste gas stream also leads to carbon oxides, as well as sulfur oxides and possibly additional formaldehyde. COS may also be a minor product.

The reaction mixture leaving the catalytic reactor is generally subject to further processing in a conventional manner. For example, the formaldehyde product can be separated in a washer (absorber), or by indirect cooling, or also by fractional cooling. For example, the washing can be performed with water, in which case a multi-stage washer can be used. An aqueous formaldehyde solution is obtained in this manner. From this solution commercial formaldehyde solutions can be prepared by distillation for immediate technical use. The formaldehyde also can be condensed out of the reaction gas together with the water that has formed. In this manner, concentrated formaldehyde solutions in common commercial form eventually can be obtained. Other ways for isolating and recovering the formaldehyde product will be apparent to those skilled in this art.

The residual gas stream, following removal of formaldehyde, can be treated in an incinerator, to combust (fully oxidize) any residual oxidizable constituents, before discharging the gas stream into the atmosphere. Alternatively, if the residual gas contains a significant amount of methanol, the gas stream can be recycled for additional treatment in the catalytic reactor.

For obtaining higher yields and selectivities in the conversion of the methanol contained in the pulp mill waste gas to formaldehyde, it may be desirable to conduct the reaction such that only a partial reaction takes place in a single pass through the reactor. For example, the pressure, temperature, composition of the starting gas mixture, the amount of catalyst and/or the rate of flow can each be varied to cause a partial conversion of the methanol-containing feed. The reactor effluent gas remaining after separation of the formaldehyde can then be recycled into the reactor. It is desirable to add to this gas an amount of pulp mill waste gas to replenish the amount of methanol that has been consumed. In this manner, a continuous circulation can be achieved. If the gas is recirculated in this manner, inert gases and other catalytic reaction products, especially carbon oxides, will concentrate in the recycled gas, and any excessive accumulation of these gases can be prevented by a continuous or discontinuous side-stream removal. It is also desirable to replace the removed exhaust gas with an equal amount of fresh gas.

Suitable bulk metal oxide catalysts for use in connection with the present invention generally constitute molybdates (Mo), chromates (Cr), vanadates (V), rhenates (Re), titinates (Ti), niobates (Nb), tungstates (W), antimonates (Sb), stannates (Sn), ceriates (Ce) and mixtures thereof. Such metal oxides also contain a wide variety of other metal species such as alkali metals (such as sodium (Na), lithium (Li), potassium (K) and cesium (Cs)), alklaine earth metals (such as calcium (Ca), barium (Ba), and magnesium (Mg)) and transition metals (such as copper (Cu), nickel (Ni), cobalt (Co), aluminum (Al), lead (Pb), bismuth (Bi), iron (Fe), zinc (Zn), cadmium (Cd), tellurium (Te), manganese (Mn)). Those skilled in the art recognize the wide variety of available bulk metal oxide catalysts.

Methods for making bulk metal oxide catalysts used in the present invention also are well known to those skilled in the art. In particular, the active catalyst can be prepared by physically blending and grinding of the metal oxides, by coprecipitation from aqueous and non-aqueous solutions containing soluble compounds of the catalyst components in the desired molar ratio, by thermal transformation, by sol-gel formation or by any other technique that provides an intimate mixture of the metal oxide constituents. For example, an aqueous solution of a water-soluble molybdenum compound (ammonium heptamolybdate) is mixed with a water-soluble iron compound (ferric chloride) and the solution is modified (e.g., by pH adjustment) to cause coprecipitation of both molybdenum and iron, using procedures well known to those skilled in the art. The coprecipitate is washed to eliminate the soluble salts formed during the coprecipitation reactions, filtered, dried, and calcined to convert the metal constituents to their active iron molybdate (oxide) form. Those skilled in the art recognize a variety of water soluble metal compounds that can be used to prepare the active catalyst. Alternatively, oxides of the respective metals may be ground together and calcined. Additional details on bulk metal oxides and bulk metal oxide catalysis can be found in Arora et al., *Journals of Catalysis*, 159, (1996) 1–13, which is incorporated herein by reference.

Those skilled in the art recognize that there exists a wide range of compounds, generally used in admixture, suitable for preparing bulk metal oxide catalysts. The following is a representative, though not exhaustive, list of possible constituents: bulk vanadates such as $PbV_2O_6$, $NaVO_3$, $Na_3VO_4$, $BiVO_4$ and other Bi—V—O family members, $AlVO_4$, $FeVO_4$, $Mg_3(VO_4)_2$, $Mg_2V_2O_7$, $CeVO_4$, $Zn_3(VO_4)_2$, $CdV_2O_7$, $Zn_2V_2O_7$, $VOPO_4$ and other V—P—O family members, $KVO_3$, $Pb_2V_2O_7$, and $TlVO_4$; bulk molybdates such as $PbMoO_4$, $Sb_2(MoO_4)_3$, $SnMoO_4$, $Ce_2(MoO_4)_3$, $CaMoO_4$, $Bi_2Mo_2O_9$, $Bi_3(FeO_4)(MoO_4)_3$ and other Bi—Mo—O family members, $Na_2MoO_4$, $MnMoO_4$, $Gd_2(MoO_4)_3$, $MgMoO_4$, $CuMoO_4$, $CoMoO_4$, $Fe_2(MoO_4)_3$, $Te_2MoO_7$, $CoMoO_4$, $Al_2(MoO_4)_3$, $Cr_2(MoO_4)_3$, and $Na_2Mo_2O_7$; bulk niobates such as $YNbO_4$, $YbNbO_4$, $LiNbO_3$, $NaNbO_3$, $KNbO_3$, $AlNbO_4$, $K_8Nb_6O_{19}$, $BiNbO_4$, and other Bi—Nb—O family members, $SbNbO_4$, $NbOPO_4$, $CaNb_2O_6$, $K_4Nb_6O_{17}$, and $KCa_2Nb_3O_{10}$; bulk tungstates such as $Li_6WO_6$, $FeWO_4$, $CoWO_4$, $MnWO_4$, $NiWO_4$, $CuWO_4$, $CaWO_4$, $Cs_2WO_4$, $Na_2WO_4$, $B_aWO_4$, $Fe_2(WO_4)_3$, $Al_2(WO_4)_3$, $SrWO_4$, $K_2WO_4$, $Na_2W_2O_7$, $Li_2WO_4$, $CsLuW_2O_8$, $BiWO_4$, and other Bi—W—O family members; bulk chromates such as $K_2CrO_4$, $K_2Cr_2O_7$, $K_2Cr_3O_{10}$, $K_2Cr_4O_{13}$, $BiCrO_4$ and other Bi—Cr—O family members; bulk rhenates such as $NaReO_4$, $Li_6ReO_4$, and $Mg(ReO_4)_2$; bulk titanates such as $Na_2TiO_4$, $NaTiO_3$, $BaTiO_4$, $BaTiO_3$, and other Ba—Ti—O family members, $Sb_2O_3$, $Sb_2O_5$, $SnO_2$ and $CeO_2$.

Bulk metal oxide catalysts are usually crystalline in nature, possess long range order, and give rise to an x-ray diffraction (XRD) pattern. The crystalline form can also usually be detected with Raman spectroscopy (often more sensitive than XRD). Further, information concerning bulk metal oxide catalysts may be found in J. Raman Spectroscopy, 21, 683–691 (1990); J. Physical Chemistry, 95(13), 5031–5041 (1991); Solid State Ionics, 45, 201–213 (1991); J. Raman Spectroscopy, 26, 397–405 (1995); and J. Chem., Soc., Faraday Trans., 92(11), 1969–1973 (1996), and *Characterization of Catalytic Materials*, edited by Israel E. Wachs, Chapter 3, pp. 47–68 (Butterworth-Heinemann, 1992) all of which are incorporated herein by reference.

In preparing a suitable bulk oxide catalyst, a period of thermal treatment is generally necessary to convert catalyst precursor species to active bulk metal oxide catalysts. Such treatment can occur either during calcination or under reaction conditions, or using some combination thereof. Under these conditions the catalyst precursor components are transformed into the active bulk metal oxide catalyst. Suitable catalyst species appear to be formed as a result of calcination at about 350° to about 850° C., preferably about 400° to about 700° C. and most preferably about 425° to about 625° C., for a period of at least about 0.5 hour, preferably for a period of about 2 to about 3 hours. The time period may depend on equipment used, as known to those skilled in the art.

As noted above, in the broad practice of the present invention, the bulk metal oxide catalyst can be either unsupported or supported. Methods for dispersing the active metal oxide catalyst on a suitable support material are known. The support material usually comprises a porous refractory oxide. Preferred are refractory oxides and other similar materials having a specific surface area of at least about 1 $m^2/g$. Most supports will have a specific surface area in the range of 1–20 $m^2/g$. Suitable support materials include such refractory oxides as zirconia, silica-alumina, magnesium oxide, alumina-silica-magnesia, silica-zirconia, alumina, silica, titania (titanium dioxide), silica-titania, silica-magnesia, silica-zirconia-titania and other combinations of such materials. Also available as a supports are amorphous and crystalline alumino-silicates, both natural and synthetic, and crystalline silicas, Most often, the support used in the invention will be relatively inert (does not adversely affect the catalyzed reactions) with respect to the catalytic composition dispersed thereon. Oxides supported on high surface area materials such as silica, alumina or refractory monoliths are commercially available. Silica often will be the best support for the bulk metal oxide.

Titania support material can be employed in the anatase or rutile form. For example, at least about 25 wt % (and generally from about 50 to about 100 wt %) of the titanium dioxide ($TiO_2$) can be in the anatase form. As recognized by those skilled in the catalytic art, titania support material may need to be judiciously evaluated since certain grades may have impurities that may interfere with catalytic activity. The same may be true of certain alumino-silicates. Normally, with recognition of the previous caveat, the titanium dioxide may be prepared by any conventional technique. The titanium dioxide used in the catalyst of this invention may be composed of substantially porous particles of a diameter of from about 0.4 to about 0.7 micron and preferably has a specific surface area of at least about 1 $m^2/g$.

The unsupported or supported catalyst, in turn, can advantageously be provided as a coating on a foamed ceramic, honeycomb or a monolithic carrier, such as those having a unitary cylindrical body with a plurality of fine, substantially parallel gas flow passages extending therethrough and connecting both end-faces of the carrier to provide a "flow-through" type of carrier. Such carriers may be prepared with known ceramic-like materials such as cordierite, silicon nitride, mullite, spodumene, sillimanite, petalite, and silica-carbide. Typical monolithic carriers are thin-walled channels which can be of any suitable cross-sectional shape and size such as trapezoidal, rectangular, square, sinusoidal, hexagonal, oval and circular. Such structures may contain from about 60 to 600 or more gas inlet openings ("cells") per square inch of cross section. The active supported or unsupported catalyst may also be provided as a layer on refractory particles such as spheres, ceramic rings, pellets or short, extruded segments of a refractory material such as alumina.

A supported bulk metal oxide catalyst can be prepared in a variety of ways as recognized by those skilled in the catalyst art. For example, an aqueous slurry of particulate bulk metal oxide (or a precursor thereof) can be applied to the support, dried and heated (calcined) to form (adhere) a catalytic material coating. The coating slurry can be prepared by mixing the metal oxide particles or precursor particles with water and ball-milling (pulverizing) the mixture to a desired particle size. The coating of catalytic material may be applied by dipping the support into the aqueous slurry of the catalyst or catalyst precursor particles. Alternatively, the catalyst precursor species, as a solution, can be incorporated onto the support by known impregnation and co-precipitation techniques, wherein the desired catalyst species are formed in part by co-precipitation directly onto the suitable support.

Preparation of active bulk metal oxide catalyst in the form of pills, pellets, granules, rings, spheres and the like by comulling techniques also is known. Particulate bulk metal oxide or metal oxide precursor species optionally may be combined with an inorganic clay binder, optionally a support material and the necessary amount of water to form a paste or dough which is extruded or pelletized, dried and heat treated (calcined) to yield active catalyst of a desired extrudate form and strength. As understood by those skilled in the art, the physical properties of the extruded materials (density, macroporosity and surface area) depend on a variety of parameters.

It often is desired that the bulk metal oxide used in accordance with the present invention have a surface area in the range of about 10 to about 150 $m^2/g$ and higher. Use of free bulk metal oxide particulates might be desirable when large catalyst volumes are needed or if the catalyst bed is operated in a fluidized state. A monolithic form or deposition of the active bulk catalyst on a catalyst support, such as on an inert ceramic support, might be preferred in applications where catalyst movement is to be avoided because of concerns about catalyst attrition and dusting, and a possible increase in pressure drop across a particulate bed. In a preferred approach, a bulk metal oxide supported catalyst, may use a ceramic or refractory inorganic carrier such as silicon carbide, silicon nitride, carborundum, steatite, alumina and the like, provided in the shape of rings or pellets. Typically, the active catalyst will be applied to a support, including an inert ceramic support in an amount to provide 1 to 20% by weight, and preferably 5 to 15%, of the supported catalyst.

Within the broad practice of the invention, the catalytic reactor can be supplied with a single catalyst composition or combinations of multiple bulk metal oxide supported or unsupported catalysts can be used.

EXAMPLE

An iron-molybdate catalyst containing iron ($Fe_2O_3$) and molybdenum ($MoO_3$) in a molar ratio (Fe:Mo) of 1.0/2.15, obtained from Perstorp, was used to oxidize methanethiol in an isothermal fixed-bed integral mode reactor operating at atmospheric pressure. The methanethiol ($CH_3SH$), diluted in helium, was supplied by Scott Specialty Gases. The reactant gas was further diluted in helium and air (Blue Valley Welding Supply, total hydrocarbons concentration <1 ppm, $H_2O$ concentration <3 ppm) and sent to the reactor through glass tubing connected with Teflon fittings. Flow rates and concentrations were controlled by two mass flow controllers (Brooks 5850 D, 1–100 sccm for helium and Omega FMA-767-V, 0–1 slpm for the reactants). The lines were heated to 70° C. for the methanethiol oxidation studies to prevent condensation. The total gas flow was maintained between 150 and 200 ml/min. The reactor was kept in a vertical position and made of 6-mm O.D. Pyrex glass. Heating tape was used in conjunction with a feedback temperature controller (Omega CN 9000) to obtain the desired reactor temperature. The catalyst (100 mg) was held at the middle of the reactor tube between a porous glass frit, pore size of 40 to 60 μm, and a glass wool plug. The catalyst sample was pretreated by heating at 500° C. for 2 to 3 hours in flowing air to remove adsorbed water on the catalyst surface prior to initiation of an experiment. The outlet of the reactor was connected to an FTIR cell (Infrared Analysis, Inc; Model #G-4-Tin-Ta-Ba-Ag), that was used to analyze the reaction products. The lines between the outlet and the cell were heated to avoid condensation of the products. The flow rate of reaction products sent to the FTIR cell was controlled by a needle valve (Nupro Company, SS-4BRG).

Analysis of the reaction products was accomplished using a Midac Inc. FTIR, (Model #101250, series 2–4). The gas was analyzed in a path gas cell (Infrared Analysis, Inc; Model # G-4-Tin-Ta-Ba-Ag), that has an effective length of 10 m and a volume of 3.1 L. The spectrometer was controlled by a microcomputer (Sprouse Scientific, model TECH- 1000 A) to provide acquisition and manipulation of the spectra: display, subtraction, zoom, etc. The spectra were obtained using 16 scans at a resolution of 0.5 $cm^{-1}$. The FTIR analysis required about 10 minutes. On one pass, 40% of the methanethiol was converted into a product containing 85% formaldehyde, 10% carbon monoxide and 5% carbon dioxide.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

What is claimed is:

1. A process for producing formaldehyde from a methanol-containing waste gas stream which comprises contacting said methanol-containing waste gas stream with a bulk metal oxide catalyst under oxidizing conditions for a time sufficient to convert at least a portion of the methanol to formaldehyde, and recovering said formaldehyde from said gas.

2. The process of claim 1 wherein said methanol-containing waste gas is produced from a pulp mill waste condensate stream.

3. The process of claim 1 wherein the bulk metal oxide catalyst is selected from the group consisting of molybdates (Mo), chromates (Cr), vanadates (V), rhenates (Re), titinates (Ti), niobates (Nb), tungstates (W) and mixtures thereof.

4. The process of claim 3 wherein the bulk metal oxide catalyst is supported on a refractory metal oxide.

5. The process of claim 3 wherein the bulk metal oxide catalyst comprises at least one member selected from the group consisting of $PbV_2O_6$, $NaVO_3$, $Na_3VO_4$, $BiVO_4$, $AlVO_4$, $FeVO_4$, $Mg_3(VO_4)_2$, $Mg_2V_2O_7$, $CeVO_4$, $Zn_3(VO_4)_2$, $CdV_2O_7$, $Zn_2V_2O_7$, $VOPO_4$, $KVO_3$, $Pb_2V_2O_7$, $TlVO_4$, $PbMoO_4$, $Sb_2(MoO_4)_3$, $SnMoO_4$, $Ce_2(MoO_4)_3$, $CaMoO_4$, $Bi_2Mo_2O_9$, $Bi_3(FeO_4)(MoO_4)_3$, $Na_2MoO_4$, $MnMoO_4$, $Gd_2(MoO_4)_3$, $MgMoO_4$, $CuMoO_4$, $CoMoO_4$, $Fe_2(MoO_4)_3$, $Te_2MoO_7$, $CoMoO_4$, $Al_2(MoO_4)_3$, $Cr_2(MoO_4)_3$, $Na_2Mo_2O_7$, $YNbO_4$, $YbNbO_4$, $LiNbO_3$, $NaNbO_3$, $KNbO_3$, $AlNbO_4$, $K_8Nb_6O_{19}$, $BiNbO_4$, $SbNbO_4$, $NbOPO_4$, $CaNb_2O_6$, $K_4Nb_6O_{17}$, $KCa_2Nb_3O_{10}$, $Li_6WO_6$, $FeWO_4$, $CoWO_4$, $MnWO_4$, $NiWO_4$, $CuWO_4$, $CaWO_4$, $Cs_2WO_4$, $Na_2WO_4$, $BaWO_4$, $Fe_2(WO_4)_3$, $Al_2(WO_4)_3$, $SrWO_4$, $K_2WO_4$, $Na_2W_2O_7$, $Li_2WO_4$, $CsLuW_2O_8$, $BiWO_4$, $K_2CrO_4$, $K_2Cr_2O_7$, $K_2Cr_3O_{10}$, $K_2Cr_4O_{13}$, $BiCrO_4$, $NaReO_4$, $Li_6ReO_4$, $Mg(ReO_4)_2$, $Na_2TiO_4$, $NaTiO_3$, $BaTiO_4$, $BaTiO_3$, $Sb_2O_3$, $Sb_2O_5$, $SnO_2$ and $CeO_2$.

6. The process of claim 5 wherein the bulk metal oxide catalyst is supported on a refractory metal oxide.

7. The process of claim 1 wherein said contacting is conducted at a temperature between 200° and 700° C.

8. The process of claim 7 wherein said contacting is conducted at a temperature between 325° and 500° C.

9. The process of claim 8 wherein said methanol-containing waste gas stream is contacted with said catalyst such that between $10^{-2}$ and $10^5$ cubic centimeters of methanol contacts a gram of catalyst per minute.

10. The process of claim 9 wherein between 0.1 and $10^4$ cubic centimeters of methanol contact a gram of catalyst per minute.

11. A process for oxidizing a waste gas stream containing oxidizable carbon-containing and sulfur-containing constituents which comprises, contacting said gas with a bulk metal oxide catalyst under oxidizing conditions for a time, and at a temperature, sufficient to convert the carbon-containing constituents to carbon oxides and the sulfur-containing constituents to sulfur oxides.

12. The process of claim 11 wherein said waste gas stream is produced from a pulp mill condensate.

13. The process of claim 11 wherein the bulk metal oxide catalyst is selected from the group consisting of molybdates (Mo), chromates (Cr), vanadates (V), rhenates (Re), titinates (Ti), niobates (Nb), tungstates (W) and mixtures thereof.

14. The process of claim 13 wherein the bulk metal oxide catalyst is supported on a refractory metal oxide.

15. The process of claim 13 wherein the bulk metal oxide catalyst comprises at least one member selected from the group consisting of $PbV_2O_6$, $NaVO_3$, $Na_3VO_4$, $BiVO_4$, $AlVO_4$, $FeVO_4$, $Mg_3(VO_4)_2$, $Mg_2V_2O_7$, $CeVO_4$, $Zn_3(VO_4)_2$, $CdV_2O_7$, $Zn_2V_2O_7$, $VOPO_4$, $KVO_3$, $Pb_2V_2O_7$, $TlVO_4$, $PbMoO_4$, $Sb_2(MoO_4)_3$, $SnMoO_4$, $Ce_2(MoO_4)_3$, $CaMoO_4$, $Bi_2Mo_2O_9$, $Bi_3(FeO_4)(MoO_4)_3$, $Na_2MoO_4$, $MnMoO_4$, $Gd_2(MoO_4)_3$, $MgMoO_4$, $CuMoO_4$, $CoMoO_4$, $Fe_2(MoO_4)_3$, $Te_2MoO_7$, $CoMoO_4$, $Al_2(MoO_4)_3$, $Cr_2(MoO_4)_3$, $Na_2Mo_2O_7$, $YNbO_4$, $YbNbO_4$, $LiNbO_3$, $NaNbO_3$, $KNbO_3$, $AlNbO_4$, $K_8Nb_6O_{19}$, $BiNbO_4$, $SbNbO_4$, $NbOPO_4$, $CaNb_2O_6$, $K_4Nb_6O_{17}$, $KCa_2Nb_3O_{10}$, $Li_6WO_6$, $FeWO_4$, $CoWO_4$, $MnWO_4$, $NiWO_4$, $CuWO_4$, $CaWO_4$, $Cs_2WO_4$, $Na_2WO_4$, $BaWO_4$, $Fe_2(WO_4)_3$, $Al_2(WO_4)_3$, $SrWO_4$, $K_2WO_4$, $Na_2W_2O_7$, $Li_2WO_4$, $CsLuW_2O_8$, $BiWO_4$, $K_2CrO_4$, $K_2Cr_2O_7$, $K_2Cr_3O_{10}$, $K_2Cr_4O_{13}$, $BiCrO_4$, $NaReO_4$, $Li_6ReO_4$, $Mg(ReO_4)_2$, $Na_2TiO_4$, $NaTiO_3$, $BaTiO_4$, $BaTiO_3$, $Sb_2O_3$, $Sb_2O_5$, $SnO_2$ and $CeO_2$.

16. The process of claim 15 wherein the bulk metal oxide catalyst is supported on a refractory metal oxide.

17. The process of claim 11 wherein said contacting is conducted at a temperature between 200° and 700° C.

18. A process for producing formaldehyde from a methanol-containing pulp mill waste gas stream which comprises contacting said methanol-containing pulp mill waste gas stream with a bulk metal oxide catalyst under oxidizing conditions to convert at least a portion of the methanol to formaldehyde, and recovering said formaldehyde from said gas.

* * * * *